United States Patent [19]
van Muiden

[11] Patent Number: 5,851,203
[45] Date of Patent: Dec. 22, 1998

[54] NEURO-MICROCATHETER

[75] Inventor: Johannes Gerardus Maria van Muiden, Peize, Netherlands

[73] Assignee: Cordis Corporation, Miami Lakes, Fla.

[21] Appl. No.: 892,562

[22] Filed: Jul. 14, 1997

Related U.S. Application Data

[63] Continuation of Ser. No. 313,740, Sep. 22, 1994, abandoned.

[30] Foreign Application Priority Data

Sep. 22, 1993 [NL] Netherlands ............... 93.01642

[51] Int. Cl.$^6$ .................................................. A61M 25/00
[52] U.S. Cl. ........................ 604/282; 604/280; 138/125
[58] Field of Search .................. 604/93, 264, 280–283; 138/124, 125, 130, 132, 144

[56] References Cited

U.S. PATENT DOCUMENTS

| | | | |
|---|---|---|---|
| 3,485,234 | 12/1969 | Stevens | 604/282 |
| 4,385,635 | 5/1983 | Ruiz . | |
| 4,405,314 | 9/1983 | Cope . | |
| 4,430,083 | 2/1984 | Ganz et al. . | |
| 4,563,180 | 1/1986 | Jervis et al. . | |
| 4,596,563 | 6/1986 | Pande | 604/280 |
| 4,636,346 | 1/1987 | Gold et al. | 604/280 |
| 4,739,768 | 4/1988 | Engelson | 604/282 |
| 4,983,169 | 1/1991 | Furukawa . | |
| 5,017,259 | 5/1991 | Kohsai . | |
| 5,037,404 | 8/1991 | Gold et al. | 604/282 |
| 5,061,257 | 10/1991 | Martinez et al. . | |
| 5,069,673 | 12/1991 | Shwab | 604/281 |
| 5,085,649 | 2/1992 | Flynn . | |
| 5,180,387 | 1/1993 | Ghajar et al. . | |
| 5,215,614 | 6/1993 | Wijkamp et al. . | |
| 5,221,270 | 6/1993 | Parker . | |
| 5,240,537 | 8/1993 | Bodicky . | |
| 5,279,596 | 1/1994 | Castaneda et al. . | |
| 5,308,342 | 5/1994 | Sepetka et al. | 604/280 |
| 5,312,356 | 5/1994 | Engelson et al. | 604/282 |
| 5,334,169 | 8/1994 | Brown et al. . | |
| 5,336,205 | 8/1994 | Zenzen et al. . | |
| 5,358,493 | 10/1994 | Schweich, Jr. et al. | 604/264 |
| 5,380,304 | 1/1995 | Parker | 604/280 |
| 5,380,307 | 1/1995 | Chee et al. | 604/264 |
| 5,454,795 | 10/1995 | Samson | 604/282 |
| 5,533,985 | 7/1996 | Wang | 604/282 |
| 5,542,937 | 8/1996 | Chee et al. | 604/280 |
| 5,554,139 | 9/1996 | Okajima | 604/264 |

FOREIGN PATENT DOCUMENTS

| | | |
|---|---|---|
| 0063859 | 3/1982 | European Pat. Off. . |
| 4032869 | 4/1992 | Germany . |
| 9407549 | 4/1994 | WIPO . |

*Primary Examiner*—Ronald Stright, Jr.
*Attorney, Agent, or Firm*—Thomas R. Vigil; Henry W. Collins

[57] ABSTRACT

The neuro-microcatheter is especially adapted for use in the small blood vessels of the brain. The neuro-microcatheter comprises a generally tubular body including a proximal portion, a transition portion and a distal portion and having at least one lumen therein extending from a distal end of the tubular body to a proximal end of the tubular body to which a connecting member can be connected. The tubular body has, in the transition portion, an outer diameter which decreases gradually, over at least part of its length, in the direction from the proximal end of the tubular body toward the distal end of the tubular body. Also, the transition portion increases in flexibility in the direction from the proximal end of the tubular body toward the distal end of the tubular body; and the transition portion has a length of between approximately 0.05 centimeter to approximately 1 meter.

14 Claims, 1 Drawing Sheet

NEURO-MICROCATHETER

This is a continuation of application Ser. No. 08/313,740 filed Sep. 22, 1994, now abandoned.

BACKGROUND OF THE INVENTION

1. Field of the Invention

The invention relates to a neuro-microcatheter especially designed for use in the tortuous, small blood vessels in the human brain. It is desirable that the distal end of such a catheter be pliable to such an extent that it can pass through very small bends, smaller than 5 mm, in the vascular system of the brain. At the same time the catheter should be sufficiently stiff towards the proximal end to transmit the longitudinal forces when introducing and manipulating the catheter. Furthermore, these qualities must be combined in a relatively long catheter, up to 1 meter in some cases, wherein the distal end must be capable of penetrating into very narrow blood vessels with a diameter considerably smaller than 1 mm.

2. Description of the Related Art

Heretofore in the non-analogous arts of angiography and angioplasty, of infusion catheters, and of cardiovascular catheters, catheters with soft tips, flexible tips and tapered tips have been proposed. Examples of these non-analogous catheters for cardiovascular procedures and of analogous ventricular catheters for use in the brain are disclosed in the following U.S. Patents and foreign patent publications:

| U.S. Pat. No. | Patentee |
| --- | --- |
| 4,385,635 | Ruiz |
| 4,405,314 | Cope |
| 4,430,083 | Ganz et al. |
| 4,563,180 | Jervis et al. |
| 4,983,169 | Furukawa |
| 5,017,259 | Kohsai |
| 5,061,257 | Martinez et al. |
| 5,085,649 | Flynn |
| 5,180,387 | Ghajar et al. |
| 5,215,614 | Wijkamp et al. |
| 5,221,270 | Parker |
| 5,240,537 | Bodicky |
| 5,279,596 | Castaneda et al. |
| 5,334,169 | Brown et al. |
| 5,336,205 | Zenzen et al. |
| German Patent Publications: | |
| DE 40 32 869 | Garcke |

The Ruiz U.S. Pat. No. 4,385,635 discloses an angiographic catheter with a soft tip. The catheter has a constant outer diameter, an intermediate zone where a tapered distal portion of a polyamide inner tube is bonded to a tapered portion of a soft, bendable, flexible and pliable elastomeric outer tube and a soft tip zone having a length of 1 to 10 millimeters.

The Jervis et al. U.S. Pat. No. 4,563,180 and the Ganz et al. U.S. Pat. No. 4,430,083 disclose infusion catheters which decrease in outer diameter toward the distal ends thereof.

The Parker U.S. Pat. No. 5,221,270, the Castaneda et al. U.S. Pat. No. 5,279,596 and the Brown et al U.S. Pat. No. 5,334,169 disclose cardiovascular catheters having braided or wound filaments, threads or wires embedded in a tubular body of the catheter.

The German published patent application DE 40 32 869 discloses the bonding of a low friction material to the cylindrical wall of a lumen in a catheter.

SUMMARY OF THE INVENTION

According to the present invention there is provided a neuro-microcatheter especially adapted for use in the small blood vessels of the brain. The neuro-microcatheter comprises a generally tubular body including a proximal portion, a transition portion and a distal portion and having at least one lumen therein extending from a distal end of the tubular body to a proximal end of the tubular body to which a connecting member can be connected. The tubular body has, in the transition portion, an outer diameter which decreases gradually, over at least part of its length, in the direction from the proximal end of the tubular body toward the distal end of the tubular body. Also, the transition portion increases in flexibility in the direction from the proximal end of the tubular body toward the distal end of the tubular body; and the transition portion has a length of between approximately 5 centimeter to approximately 1 meter.

During catheterization, the catheter is introduced into a relatively wide blood vessel and advanced from there to even narrower vessels. Toward the proximal end the thickness of the catheter may therefore be greater, without limiting the accessibility to very small blood vessels. Because of the somewhat greater thickness close to the proximal end, the neuro-microcatheter can be manipulated properly by engagement of the proximal end thereof.

In order to be able to use the catheter according to the invention with a metal guide wire or one coated with polytetrafluorethylene, which obviously will have a very small diameter, the lumen is bounded by a layer of low friction material.

The friction between the guide wire and the catheter will consequently be so little that, even in case of a very tortuous passage of the catheter in the vascular system in the brain, the guide wire will not become stuck inside the catheter. The layer of material characterized by low friction can, for instance, be made of polytetrafluorethylene or polyethylene, which at the same time can withstand aggressive chemotherapeutics or wear from the guide wire.

A desired increase in the pliability toward the distal end is already due to a decrease in the diameter but is additionally enhanced, preferably by providing the neuro-microcatheter with a relatively stiff and a relatively flexible layer of material and by constructing the neuro-microcatheter with a cross-section of the stiff layer of material which decreases, relative to the flexible layer of material, toward the distal end of the neuro-microcatheter.

By using relatively stiff material close to the proximal end and then, in increasing manner, more pliable material toward the distal end, a desired, great difference in flexibility of the distal end and the proximal end can be achieved.

The decrease in diameter and the increase in flexibility can be obtained by providing the flexible layer of material with a substantially constant thickness over the length of the catheter and by controlling the thickness of the stiff layer of material so that it decreases from the proximal toward the distal end.

In order to achieve a good pressure resistance and a good torsional resistance at least close to the proximal end, a reinforcing layer braided or wound of threads or filaments is provided.

To reduce axial flexibility at the distal end, the pitch of the braided or wound threads or filaments increases toward the distal end.

One preferred neuro-microcatheter constructed according to the teachings of the present invention, preferably will have a diameter which decreases from 1.0 or 0.8 mm to 0.75 mm or 0.65 mm.

BRIEF DESCRIPTION OF THE DRAWINGS

The invention will be explained in greater detail with reference to the four examples of embodiments shown schematically in the attached drawings wherein each of the FIGS. 1–4 illustrates schematically a basic body of a catheter constructed according to the teachings of the present invention, with the proximal end on the right hand side and the distal end on the left hand side.

DESCRIPTION OF THE PREFERRED EMBODIMENT(S)

Figure 1:
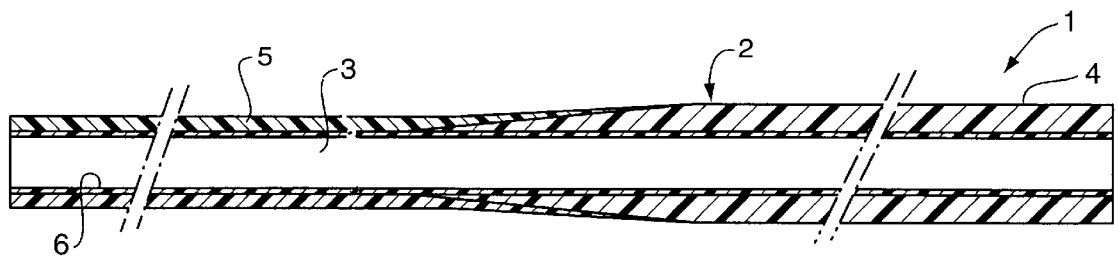
FIG. 1 is a longitudinal sectional view of one embodiment of the neuro-microcatheter constructed according to the teachings of the present invention.

The basic body 2 of the catheter 1 shown in FIG. 1 comprises one lumen 3 which runs from the proximal end, to which a connecting member, not shown here, has been attached, to the distal end. As shown in FIG. 1, the diameter of the basic body 2 gradually decreases in a transition portion or zone from the proximal end towards the distal end.

The basic body 2 is made up of a relatively stiff layer of material 4 and a relatively flexible layer of material 5. The cross-section of the stiff layer of material 4 decreases in relation to the flexible layer of material 5 in a transition zone. This transition zone can vary in length from 5 centimeter to up to 1 meter and typically has a length of several tens of centimeters, for example from approximately 5 cm to approximately 50 cm. Close to the proximal end, the stiff layer of material 4 has a constant cross-section and close to the distal end the flexible layer of material 5 has a constant cross-section.

The gradual transition from the one layer of material 4 to the other 5, can be achieved by manufacturing the basic body 2 by intermittent extrusion. The supply of the stiff material 4 is gradually reduced, while the supply of the flexible material 5 is gradually increased, In order to achieve the reduction in diameter, the reduction in the supply of the stiff material 4 will, however, be set at a rate less than the rate of increase in the supply of the flexible material 5.

The gradual reduction in outside diameter from the proximal toward the distal end can also be achieved by increasing the carrying velocity of the extrusion product, e.g., increasing the velocity of the pulling of the material being extruded, during the transition from the stiff to the flexible material.

The lumen 3 is bounded by a layer 6 made of a low friction material, such as polytetrafluorethylene or polyethylene, in order to achieve minimal friction with respect to a guide wire to be advanced through the lumen 3.

Figure 2:
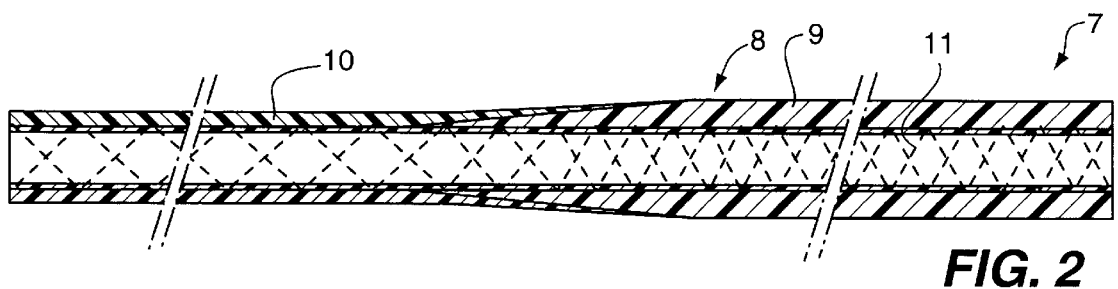
FIG. 2 is a longitudinal sectional view of another embodiment of the neuro-microcatheter constructed according to the teachings of the present invention.

The catheter 7, as shown in FIG. 2, is basically similar to the catheter 1, as shown in FIG. 1. Also, in this case the basic body 8 comprises one lumen, made of a stiff layer of material 9 and a flexible layer of material 10, which decreases in diameter toward the distal end of the basic body 8.

The catheter 7 further comprises a braided or wound reinforcing layer 11 of metal or plastic threads or filaments. As shown in FIG. 2, the pitch of the braided or wound reinforcing layer is smaller at the proximal end than at the distal end, but, with another embodiment, one can also opt for the pitch to be constant from the proximal to the distal end of the catheter. In this case, the word pitch is understood to mean the distance between the threads or filaments. By using a smaller pitch close to the proximal end, the number of threads per unit length is greater, so that the reinforcing layer contributes more to the torsional resistance of the catheter than at the distal end. At the distal end, the reinforcing layer contributes more to the reduction in axial flexibility due to the larger pitch.

Figure 3:
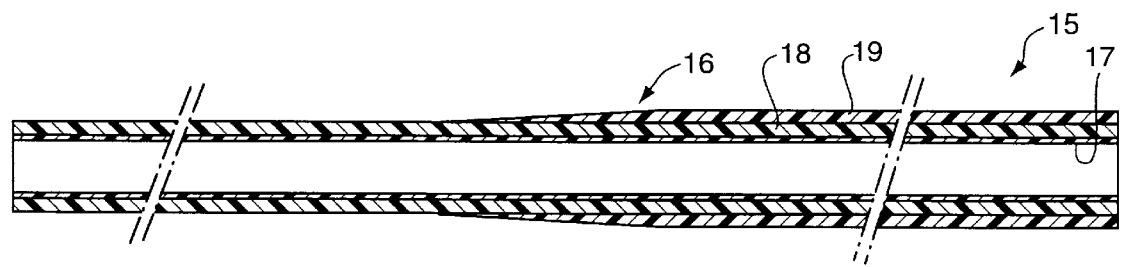
FIG. 3 is a longitudinal sectional view of a further embodiment of the neuro-microcatheter constructed according to the teachings of the present invention.

The catheter 15 illustrated in FIG. 3 comprises a basic body 16 which has been made slightly different from the catheter 1 in FIG. 1. The catheter 15 also comprises one lumen 17, a flexible layer of material 18 and a stiff layer of material 19. However, the thickness of the flexible layer of material 18 is constant over the entire length of the basic body 16, whereas the thickness of the stiff layer of material 19 reduces to zero toward the distal end. Consequently, a change in the flexibility and the thickness of the catheter is achieved. The lumen is bounded by a layer with good frictional properties like, for instance, polytetrafluorethylene or polyethylene of between approximately 0.02 and 0.3 mm, the lumen having a diameter of approximately 0.53 mm.

Figure 4:
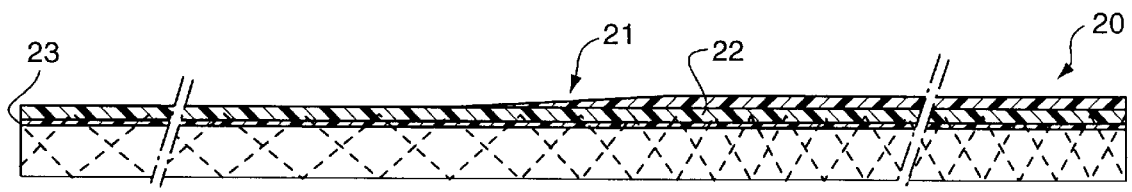
FIG. 4 is a longitudinal sectional view of still another embodiment of the neuro-microcatheter constructed according to the teachings of the present invention.

The catheter 20 of FIG. 4 has basically the same construction again as the one in FIG. 3, which, however, once again includes a reinforcing layer 22 that has been incorporated into the basic body 21 of which the threads can have an increasing pitch toward the distal end.

In the catheter 20, a layer 23 with good frictional properties has been applied. As stated above, this layer preferably comprises a polytetrafluorethylene layer or a polyethylene layer.

For the stiff layer of a material a suitable polyurethane or a low pressure polyethylene can be chosen, while for the flexible layer also a polyurethane, but in that case of a composition which displays little stiffness, or a polyethylene with vinyl acetate can be chosen.

According to the teachings of the present invention, a neuro-microcatheter is provided, suitable for use in blood vessels of the brain, which has a considerable length including a transition zone with a length between 5 cm and 1 meter in which there is a gradual decrease in diameter and a gradual increase in flexibility in the direction from the proximal end toward the distal end and a very small diameter of less than 1 mm. In one preferred embodiment, from the proximal end to the distal end, the diameter can decrease from approximately 1 mm to approximately 0.7 mm. The wall thickness of the catheter can in that case be in the order of approximately 0.1 mm, so that the inside diameter of the lumen can be approximately 0.5 mm. In the transition zone, the outer diameter reduces from an outer diameter of approximately 0.97–0.81 mm to an outer diameter of approximately 0.73–0.65 mm.

I claim:

1. A neuro-microcatheter especially adapted for use in the small blood vessels of the brain, said neuro-microcatheter comprising a generally tubular body including a proximal portion, a transition portion and a distal portion and having at least one lumen therein extending from a distal end of said tubular body to a proximal end of said tubular body to which a connecting member can be connected, said lumen having a constant diameter over substantially its entire length and being coated over substantially its entire length with a low friction material, said tubular body comprising a relatively stiff layer of material in said proximal portion and a relatively flexible layer in said distal portion, said tubular body having in said transition portion an outer diameter which decreases continuously and gradually, over a substantial portion of its length, in the direction from said proximal end of said tubular body toward said distal end of said tubular body, said stiff layer of material extending from said proximal portion into said transition portion where it has a wall thickness which decreases as it extends into said transition portion and reduces to zero toward said distal end of said tubular body, said flexible layer of material extending the substantial length of said tubular body and having a wall thickness which is substantially constant over substantially the entire length of said tubular body, said transition portion increasing in flexibility in the direction from said proximal end of said tubular body toward said distal end of said tubular body, a reinforcing layer in a said flexible layer, braided or wound, of threads or filaments situated within said tubular body, and said transition portion having a length between at least 5 centimeters and approximately 1 meter.

2. The neuro-microcatheter of claim 1 wherein said layer of low friction material is a layer of polytetrafluorethylene material.

3. The neuro-microcatheter of claim 1 wherein said layer of low friction material is a layer of polyethylene material.

4. The neuro-microcatheter of claim 1 wherein said transition portion has a length of approximately 50 cm.

5. The neuro-microcatheter of claim 1 wherein said stiff layer of material has a constant cross-section close to said proximal end and said flexible layer of material has a constant cross-section close to said distal end.

6. The neuro-microcatheter of claim 1 wherein the wall thickness of said stiff layer of material is constant over a substantial portion of a proximal portion of said tubular body and has a tapered portion which tapers to zero thickness in said transition portion between said proximal portion and said distal portion of said tubular body and wherein the wall thickness of said flexible layer of material is constant over a substantial portion of said distal portion of said tubular body.

7. The neuro-microcatheter of claim 1 wherein said stiff layer of material is made of polyurethane.

8. The neuro-microcatheter of claim 1 wherein said stiff layer of material is made of a low pressure polyethylene.

9. The neuro-microcatheter of claim 1 wherein said flexible layer of material is made of a flexible polyurethane.

10. The neuro-microcatheter of claim 1 wherein said flexible layer of material is made of polyethylene with vinyl acetate.

11. The neuro-microcatheter of claim 1 wherein said braided or wound threads or filaments have a pitch that increases in said transition portion toward said distal end of said tubular body.

12. The neuro-microcatheter of claim 1 wherein the diameter of said tubular body decreases from approximately 1.0 mm to approximately 0.75 mm. over the length of said tubular body.

13. The neuro-microcatheter of claim 1 wherein the diameter of said tubular body decreases from approximately 0.8 mm to approximately 0.65 mm. over the length of said tubular body.

14. A neuro-microcatheter especially adapted for use in the small blood vessels of the brain, said neuro-microcatheter comprising a generally tubular body including a proximal portion, a transition portion and a distal portion and having at least one lumen therein extending from a distal end of said tubular body to a proximal end of said tubular body to which a connecting member can be connected, said lumen having a constant diameter over substantially its entire length and being coated over substantially its entire length with a low friction material, said tubular body comprising a relatively stiff external layer of material in said proximal portion and a relatively flexible internal layer extending the length of said tubular body, said tubular body having in said transition portion an outer diameter which decreases gradually, over a substantial portion of its length, in the direction from said proximal end of said tubular body toward said distal end of said tubular body, said stiff external layer of material extending from said proximal portion into said transition portion where it has a cross-section which decreases as it extends into said transition portion, said transition portion increasing in flexibility in the direction from said proximal end of said tubular body toward said distal end of said tubular body, a reinforcing layer in said flexible layer, braided or wound, of threads or filaments situated within said tubular body and said transition portion having a length between at least 5 centimeters and approximately 1 meter.

* * * * *